United States Patent
Suzuki et al.

(10) Patent No.: US 11,319,261 B2
(45) Date of Patent: May 3, 2022

(54) METHOD FOR PRODUCING CONJUGATED DIENE

(71) Applicant: KURARAY CO., LTD., Kurashiki (JP)

(72) Inventors: Takahiro Suzuki, Kurashiki (JP); Kosuke Senda, Kamisu (JP); Yutaka Suzuki, Otemachi (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 16/098,727

(22) PCT Filed: Apr. 26, 2017

(86) PCT No.: PCT/JP2017/016567
§ 371 (c)(1),
(2) Date: Nov. 2, 2018

(87) PCT Pub. No.: WO2017/191794
PCT Pub. Date: Nov. 9, 2017

(65) Prior Publication Data
US 2019/0135714 A1    May 9, 2019

(30) Foreign Application Priority Data

May 6, 2016 (JP) .............................. JP2016-092951

(51) Int. Cl.
*C07C 1/24* (2006.01)
*C07C 11/18* (2006.01)
*C07B 61/00* (2006.01)

(52) U.S. Cl.
CPC ............... *C07C 1/24* (2013.01); *C07C 11/18* (2013.01); *C07B 61/00* (2013.01); *C07C 2521/06* (2013.01); *C07C 2527/053* (2013.01)

(58) Field of Classification Search
None
See application file for complete search history.

(56) References Cited

U.S. PATENT DOCUMENTS

| | | | |
|---|---|---|---|
| 3,714,285 A | 1/1973 | Mueller et al. | |
| 3,809,727 A * | 5/1974 | Johnson | C07C 1/24 585/609 |
| 4,053,536 A | 10/1977 | Hughes | |
| 6,180,555 B1 * | 1/2001 | Szabo | B01J 21/066 502/217 |
| 2010/0113846 A1 * | 5/2010 | McAuliffe | C07C 1/2078 585/16 |
| 2018/0290947 A1 * | 10/2018 | Suzuki | C07C 29/44 |

FOREIGN PATENT DOCUMENTS

| | | |
|---|---|---|
| CN | 105152832 | 12/2015 |
| JP | 47-1571 A | 1/1972 |
| JP | 47-14105 | 8/1972 |
| JP | 47014105 A * | 8/1972 |
| JP | 50-1003 B | 1/1975 |
| JP | 52-36603 A | 3/1977 |
| JP | 56033033 A * | 4/1981 |
| JP | 57-130928 A | 8/1982 |
| JP | 59-6181 B2 | 2/1984 |
| JP | 1-288339 A | 11/1989 |
| JP | 5-293375 A | 11/1993 |
| JP | 2013-75877 A | 4/2013 |
| JP | WO 2016/194983 A1 | 12/2016 |
| RU | 2116286 C1 | 7/1998 |
| RU | 2368593 C1 | 9/2009 |

OTHER PUBLICATIONS

Machine translation JP4714105A. Aug. 4, 1972. (Year: 1972).*
Machine translation JP5633033A. Apr. 3, 1981 (Year: 1981).*
Okuhara et al. Oxide Catalysts in Solid-state Chemistry. 2006 John Wiley & Sons. Encyclopedia of Inorganic Chemistry, 1-21. (Year : 2006).*
International Search Report dated Jun. 6, 2017 in PCT/JP2017/016567 filed Apr. 26, 2017.
An Extended European Search Report dated Dec. 6. 2019, in the corresponding European patent application.
Fangli Jing, et al., "Al-doped SBA-15 Catalysts for Low Temperature Dehydration of 1,3-Butanediol into Butadiene", CHEMCATCHEM, vol. 9, No. 2, Nov. 29, 2016 (Nov. 29, 2016), pp. 258-262, XP055647702, DE.
Satu Silver, et al., "Towards Benign Synthesis of Indenes from Indanones: Zinc-Mediated Allylation of Ketones in Aqueous Media as a Source of Substituted Indenyl Ligand Precursors", European Journal of Organic Chemistry, vol. 2005, No. 6, Mar. 1, 2005 (Mar. 1, 2005), pp. 1058-1081, XP055647892, DE.
Office Action dated Feb. 10, 2020 in Russian Patent Application No. 2018138691 (064335) filed Apr. 26, 2017 with English translation, 12 pages.
Office Action dated Jan. 7, 2021, in Chinese Patent Application No. 201780027377.8.

* cited by examiner

*Primary Examiner* — Philip Y Louie
(74) *Attorney, Agent, or Firm* — Oblon, McClelland, Maier & Neustadt, L.L.P.

(57) ABSTRACT

Provided is a method of producing a conjugated diene, including a step of dehydrating a γ,δ-unsaturated alcohol in the presence of a solid acid catalyst having a Hammett acidity function ($H_0$) of −12.2 or less.

8 Claims, No Drawings

METHOD FOR PRODUCING CONJUGATED DIENE

TECHNICAL FIELD

The present invention relates to a method for producing a conjugated diene. In more detail, the present invention relates to a method for producing a conjugated diene through dehydration of a γ,δ-unsaturated alcohol.

BACKGROUND ART

As a production method of a conjugated diene through dehydration of a γ,δ-unsaturated alcohol, there is known a method in which 3-methyl-3-buten-1-ol is subjected to vapor phase dehydration in the presence of a catalyst of phosphoric acid supported on pumice or calcium phosphate (see PTLs 1 and 2). Such a method involved such a problem that a large quantity of a heat source must be used for the purpose of vaporizing the raw material, or the produced conjugated diene is polymerized on the catalyst surface in a high-temperature environment, so that the catalytic activity is lowered.

As a method for solving the aforementioned problem, it is known that by adopting a dehydration reaction in a liquid phase system, the reaction temperature is suppressed. For example, PTL 3 discloses a method in which isoprene monool or the like is allowed to react in a liquid phase under pressure at a reaction temperature of 100 to 180° C. in the presence of a homogenous acid catalyst. However, in the case of adopting the foregoing method, a treatment of the acid waste fluid is needed from the viewpoint of environmental protection, so that the process becomes complicated.

As a method in which not only a high reaction temperature is not needed, but also the treatment of the acid waste fluid is not problematic, there is a method of using a catalyst functioning as a solid acid in the reaction system. For example, PTL 4 describes a method of obtaining isoprene through dehydration of 3-methyl-3-buten-1-ol in the presence of a molybdenum catalyst. However, it may not be said that the yield by the foregoing method is satisfactory, and further improvements are required.

CITATION LIST

Patent Literature
  PTL 1: JP 47-1571 A
  PTL 2: JP 50-1003 B
  PTL 3: JP 47-14105 A
  PTL 4: U.S. Pat. No. 4,053,536

SUMMARY OF INVENTION

Technical Problem

A problem of the present invention is to provide a method capable of producing a conjugated diene in a good yield under mild conditions through dehydration of a γ,δ-unsaturated alcohol.

Solution to Problem

The present inventors made extensive and intensive investigations. As a result, it has been found that a conjugated diene is obtained in a high yield through dehydration of a γ,δ-unsaturated alcohol in the presence of a solid acid catalyst, a Hammett acidity function ($H_0$) of which is a specified value, thereby leading to accomplishment of the present invention.

The present invention provides the following [1] to [6].

[1] A production method of a conjugated diene, including a step of dehydrating a γ,δ-unsaturated alcohol in the presence of a solid acid catalyst having a Hammett acidity function ($H_0$) of −12.2 or less.

[2] The production method of [1], wherein the solid acid catalyst is an oxoacid-supported metal oxide.

[3] The production method of [1], wherein the solid acid catalyst is a sulfuric acid-supported metal oxide or a tungstic acid-supported metal oxide.

[4] The production method of [1], wherein the solid acid catalyst is sulfated zirconia.

[5] The production method of any of [1] to [4], wherein a solvent is allowed to coexist.

[6] The production method of [5], wherein the solvent is an aliphatic hydrocarbon.

[7] The production method of any of [1] to [6], wherein the γ,δ-unsaturated alcohol is 3-methyl-3-buten-1-ol.

Advantageous Effects of Invention

In accordance with the production method of the present invention, a conjugated diene can be produced in a good yield under mild conditions through dehydration of a γ,δ-unsaturated alcohol.

DESCRIPTION OF EMBODIMENTS

The production method of the present invention includes a step of dehydrating a γ,δ-unsaturated alcohol in the presence of a solid acid catalyst having a Hammett acidity function ($H_0$) of −12.2 or less.

The γ,δ-unsaturated alcohol serving as a raw material in the production method of the present invention is preferably one represented by the following general formula (I) (hereinafter referred to as "γ,δ-unsaturated alcohol (I)").

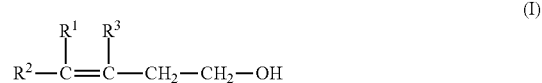

(I)

In the formula, $R^1$, $R^2$, and $R^3$ each independently represent a hydrogen atom or an alkyl group having 1 to 10 carbon atoms, and $R^1$ and $R^3$ may be connected to each other to form a ring.

By dehydrating the γ,δ-unsaturated alcohol (I), a conjugated diene represented by the following general formula (II) is obtained.

(II)

In the formula, $R^1$, $R^2$, and $R^3$ are those defined above.

(γ,δ-Unsaturated Alcohol (I))

Examples of the alkyl group having 1 to 10 carbon atoms, which $R^1$, $R^2$, and $R^3$ each independently represent, include a methyl group, an ethyl group, various propyl groups (the wording "various" means that all of a linear group and a branched group are included; hereinafter the same), various butyl groups, various hexyl groups, various octyl groups, and various decyl groups. Above all, an alkyl group having 1 to 5 carbon atoms is preferred, an alkyl group having 1 to 3 carbon atoms is more preferred, and a methyl group is still more preferred.

As the ring in the case where $R^1$ and $R^3$ are connected to each other to form a ring, rings having 5 to 10 carbon atoms, such as a cyclopentene ring, a cyclohexene ring, and a cyclooctene ring, are preferred, and a cyclohexene ring is more preferred.

As for $R^1$, $R^2$, and $R^3$, it is preferred that at least one of $R^1$ and $R^2$ is a hydrogen atom, and $R^3$ is a hydrogen atom or an alkyl group having 1 to 10 carbon atoms; and it is more preferred that all of $R^1$ and $R^2$ are a hydrogen atom, and $R^3$ is a hydrogen atom or an alkyl group having 1 to 10 carbon atoms. Preferred alkyl groups are those mentioned above.

Specific examples of the γ,δ-unsaturated alcohol (I) include those mentioned below.

(1) 3-Buten-1-ol in which all of $R^1$, $R^2$, and $R^3$ are a hydrogen atom.

(2) 3-Methyl-3-buten-1-ol that is an example in which $R^1$ and $R^2$ are a hydrogen atom, and $R^3$ is an alkyl group having 1 to 10 carbon atoms.

(3) 3-Methyl-3-penten-1-ol and 3-methyl-3-hexen-1-ol that are an example in which at least one of $R^1$ and $R^2$ is a hydrogen atom, and $R^3$ is an alkyl group having 1 to 10 carbon atoms.

(4) 3,4-Dimethyl-3-penten-1-ol and 3,4-dimethyl-3-hexen-1-ol that are an example in which all of $R^1$, $R^2$, and $R^3$ are an alkyl group having 1 to 10 carbon atoms.

(5) Cyclohexene-1-ethanol that is an example in which $R^2$ is a hydrogen atom, and $R^1$ and $R^3$ are connected to each other to form a ring.

Above of all, 3-methyl-3-buten-1-ol is preferred.

(Solid Acid Catalyst)

The solid acid catalyst which is used for the production method of the present invention has a Hammett acidity function ($H_0$) of −12.2 or less. With respect to a certain acid-base indicator B, when a base type is designated as "B", and an acid type is designated as "BH+", the Hammett acidity function of an acid is defined according to the following equation, and for example, in the case of 100% sulfuric acid, $H_0$=−11.93.

$$H_0 = pK_a + \log([B]/[BH+])$$

In the case of a Lewis acid, the Hammett acidity function is defined according to the following equation while designating a Lewis acid site as "A".

$$H_0 = pK_a + \log([B]/[AB])$$

The value of $H_0$ can be, for example, determined by the amine titration method or the like.

In the production method of the present invention, by using the acid catalyst having a Hammett acidity function ($H_0$) of −12.2 or less, the reactivity is improved, and the conjugated diene can be produced in a high yield. In addition, by using the solid catalyst, not only corrosion of an apparatus and so on and generation of an acidic waste fluid can be suppressed, but also it becomes easy to perform separation and recovery/regeneration/reuse of the catalyst from the reaction system.

The solid acid catalyst having a Hammett acidity function ($H_0$) of −12.2 or less is preferably an oxoacid-supported metal oxide. Examples of the oxoacid-supported metal oxide include sulfuric acid-supported metal oxides, such as sulfated tin(IV) oxide ($SO_4/SnO_2$, $H_0$=−18.0), sulfated zirconia ($SO_4/ZrO_2$, $H_0$=−16.1), sulfated hafnia ($SO_4/HfO_2$, $H_0$=−16.0), sulfated titania ($SO_4/TiO_2$, $H_0$=−14.6), sulfated alumina ($SO_4/Al_2O_3$, $H_0$=−14.6), sulfated iron(III) oxide ($SO_4/Fe_2O_3$, $H_0$=−13.0), and sulfated silica ($SO_4/SiO_2$, $H_0$=−12.2); tungstic acid-supported metal oxides, such as tungstated tin(IV) oxide ($WO_3/SnO_2$, $H_0$=−13.3), tungstated zirconia ($WO_3/ZrO_2$, $H_0$=−14.6), tungstated titania ($WO_3/TiO_2$, $H_0$=−13.1), and tungstated iron(III) oxide ($WO_3/Fe_2O_3$, $H_0$=−12.5); and molybdic acid-supported metal oxides, such as molybdated zirconia ($MoO_3/ZrO_2$, $H_0$=−13.3).

Among the aforementioned oxoacid-supported metal oxides, sulfuric acid-supported metal oxides or tungstic acid-supported metal oxides are preferred; sulfuric acid-supported metal oxides or tungstic acid-supported metal oxides of $H_0$=−14.0 or less are more preferred; sulfuric acid-supported metal oxides or tungstic acid-supported metal oxides of $H_0$=−16.0 or less are still more preferred; and sulfated zirconia is yet still more preferred.

From the viewpoint of availability, it is preferred to use a solid acid catalyst of $H_0$=−20.0 or more.

In the aforementioned solid acid catalyst, a BET specific surface area as the nitrogen adsorption specific surface area as measured in conformity with the "Determination of the specific surface area of powders (solids) by gas adsorption" described in JIS Z8830:2001 is preferably 20 to 800 m$^2$/g, more preferably 25 to 600 m$^2$/g, and still more preferably 50 to 500 m$^2$/g. When the BET specific surface area falls within the aforementioned range, a satisfactory catalytic activity is obtained, and a selectivity of the conjugated diene is improved.

The solid acid catalyst may be used after performing aging. By using the aged solid acid catalyst, a high catalytic activity can be exhibited. An aging time is typically 0.5 to 5 hours, and preferably 1 to 3 hours. In addition, an aging temperature is typically 100 to 300° C., and preferably 130 to 150° C. In the case where the temperature is too low, drying of the catalyst is liable to be not sufficiently achieved. In addition, in the case where the temperature is too high, there is a possibility that an unpredicted change in catalyst structure is generated, and such is not desired so much.

(Solvent)

Though the production method of the present invention can be performed in the absence of a solvent, it is preferably performed in the coexistence of a solvent. As the solvent to be used, for example, aliphatic hydrocarbons, such as octane, nonane, decane, kerosene, and a liquid paraffin; and aromatic hydrocarbons, such as xylene, toluene, and a high boiling aromatic material are preferred, with aliphatic hydrocarbons being more preferred. By performing the reaction in the presence of the solvent, attachment of high-boiling by-products to the solid acid catalyst can be suppressed, and the catalytic activity can be kept high.

A use amount of the solvent in the reaction system is preferably 80 to 99% by mass, more preferably 85 to 97.5% by mass, and still more preferably 90 to 95% by mass. When the use amount of the solvent in the reaction system falls within the range of from 80 to 99% by mass, a load to a stirring device is suppressed. In addition, the production of high-boiling by-products is suppressed, and not only the selectivity of the conjugated diene can be enhanced, but also the conversion of the γ,δ-unsaturated alcohol can be kept high. In general, it is preferred to charge the solvent into a reactor before commencement of the reaction, thereby allowing its amount to fall within the aforementioned range.

An existent amount of the solid acid catalyst in the reaction system is preferably 1 to 20% by mass, more preferably 2.5 to 15% by mass, and still more preferably 5 to 10% by mass. This amount is adjustable by, for example, the use amount of the solvent or the like. When the existent amount of the solid acid catalyst in the reaction system falls within the range of from 1 to 20% by mass, the production of high-boiling by-products is suppressed, and not only the selectivity of the conjugated diene can be enhanced, but also the conversion of the γ,δ-unsaturated alcohol can be kept high. In general, it is preferred to charge the solid acid catalyst into a reactor before commencement of the reaction, thereby regulating its amount to the aforementioned existent amount.

(Reaction Conditions, etc.)

In the production method of the present invention, a reaction temperature is preferably 100 to 210° C., more preferably 115 to 200° C., and still more preferably 120 to 190° C. When the reaction temperature is 100° C. or higher, a thoroughly high reaction rate is obtained, and the conjugated diene can be obtained in a high selectivity. In addition, when the reaction temperature is 210° C. or lower, a side reaction of the produced conjugated diene is suppressed, leading to an improvement in yield, and in addition to that, the use amount of a heat source can be suppressed. Thus, such is economically advantageous.

In the production method of the present invention, a reaction pressure is preferably 0.05 to 2.0 MPa, more preferably 0.075 to 1.5 MPa, and still more preferably 0.09 to 1.0 MPa. When the reaction pressure is less than 0.05 MPa, there is a case where it is difficult to obtain a satisfactory reaction temperature.

In the production method of the present invention, it is preferred to carry out the reaction in an inert gas atmosphere of nitrogen, argon, or the like.

In the production method of the present invention, from the viewpoint of making the reaction results stable, it is preferred to carry out the reaction in a so-called reactive distillation mode in which the solid acid catalyst having an $H_0$ of −12.2 or less and the solvent are charged, the γ,δ-unsaturated alcohol is continuously fed into a vessel regulated at a predetermined temperature and a predetermined pressure, and the produced conjugated diene and water are continuously distilled out the reaction system. A total amount of the conjugated diene and water distilled out the reactor (a value expressed into a liquid material obtained by cooling after distillation) is preferably 0.8 to 1.2 times, and more preferably 0.9 to 1.1 times of the mass of the γ,δ-unsaturated alcohol to be fed into the reactor per unit time.

EXAMPLES

The present invention is hereunder described in more detail by reference to Examples, but it should be construed that the present invention is by no means by these Examples.

In each of the Examples, the gas chromatography analysis was carried out under the following conditions.

[Gas Chromatography Analysis Conditions]

Analytical instrument: GC14A (manufactured by Shimadzu Corporation)

Detector: FID (hydrogen flame ionization detector)

Column used: DB-1 (30 m, film thickness: 5 μm) (manufactured by J&W Scientific)

Analysis conditions: Injection inlet temperature: 280° C., detector temperature: 280° C.

Temperature rise conditions: 40° C. (kept for 10 minutes) (temperature raised at 5° C./min) 250° C. (kept for 4 minutes)

Example 1

A stirrer, 28.7 g of a liquid paraffin, and 3.1 g of sulfated zirconia (reference catalyst: JRC-SZ-1, $H_0$=−16.1, BET specific surface area: 67.0 m$^2$/g) were charged in a 100-mL three-necked flask equipped with a condenser tube, and after purging the system with nitrogen, heating and stirring (at 800 rpm) were commenced under atmospheric pressure. One hour after the internal temperature had reached 130° C., 29.3 g in total of 3-methyl-3-buten-1-ol was fed at a rate of 4.9 g/hr into the flask, and a distillate was distilled in a reactive distillation mode into a 50-mL flask receiver of the outside of the system, thereby recovering 27.4 g of a distillation fraction.

When the distillation of the reactant quieted down, heating was stopped to terminate the reaction. As a result of analyzing the organic layer of the receiver and the reaction solution within the reactor by means of gas chromatography, the conversion of 3-methyl-3-buten-1-ol was 91.1%, and the selectivity of isoprene was 81.9%. In addition, the selectivity of isobutene as a by-product was 1.1%, the selectivity of 1,1-dimethyl-2-propen-1-ol as a by-product was 10.7%, the selectivity of β-methyldihydropyrane as a by-product was 0.4%, and the selectivity of an isoprene dimer as a by-product was 0.3%.

Example 2

The same operations as in Example 1 were followed, except that the catalyst was changed to 3.1 g of tungstated zirconia (manufactured by Daiichi Kigenso Kagaku Kogyo Co., Ltd., $H_0$=−14.6, BET specific surface area: 52.5 m$^2$/g). The conversion of 3-methyl-3-buten-1-ol was 88.6%, and the selectivity of isoprene was 67.9%. In addition, the selectivity of isobutene as a by-product was 0.8%, the selectivity of 1,1-dimethyl-2-propen-1-ol as a by-product was 8.6%, the selectivity of β-methyldihydropyrane as a by-product was 0.5%, and the selectivity of an isoprene dimer as a by-product was 1.2%.

Comparative Example 1

The same operations as in Example 1 were followed, except that the catalyst was changed to 3.1 g of Nafion (a registered trademark) ($H_0$=−12.0, BET specific surface area: 0.02 m$^2$/g or less). The conversion of 3-methyl-3-buten-1-ol was 95.8%, and the selectivity of isoprene was 27%.

Comparative Example 2

The same operations as in Example 1 were followed, except that the catalyst was changed to 3.1 g of γ-alumina ("E30N4", manufactured by JGC Catalysts and Chemicals Ltd., $H_0$−5.5, BET specific surface area: 186 m$^2$/g). However, the distillation of the reactant was not found, and the production of isoprene was not observed. As a result of analyzing the reaction solution within the reactor, the conversion of 3-methyl-3-buten-1-ol was 23.7%.

By using the solid acid catalyst of $H_0$=12.2 or less, the target conjugated diene could be produced in a high yield under mild conditions.

INDUSTRIAL APPLICABILITY

The conjugated diene which is obtained by the production method of the present invention is useful as various chemical products and polymer raw materials, and so on.

The invention claimed is:

1. A method of producing a conjugated diene, comprising:
preparing a mixture consisting of at least one solvent and an aged solid acid catalyst;
heating the mixture to a dehydration reaction temperature;
continuously adding a γ,δ-unsaturated alcohol to the mixture at the dehydration reaction temperature;

dehydrating the γ,δ-unsaturated alcohol to obtain the conjugated diene and water; and continuously removing the conjugated diene and the water from the mixture;

wherein a Hammett acidity function ($H_0$) of the aged solid catalyst is −12.2 or less, a BET surface area of the aged solid catalyst is from 20 $m^2/g$ to 800 $m^2/g$, a total amount of the conjugated diene and water removed from the mixture is 0.8 to 1.2 times the mass of the γ,δ-unsaturated alcohol, the at least one solvent is selected from the group consisting of aliphatic hydrocarbons and aromatic hydrocarbons, and an amount of the at least one solvent in the mixture is from 80 to 99% by mass.

2. The method according to claim 1, wherein the solid acid catalyst is an oxoacid-supported metal oxide.

3. The method according to claim 1, wherein the solid acid catalyst is a sulfuric acid-supported metal oxide or a tungstic acid-supported metal oxide.

4. The method according to claim 1, wherein the solid acid catalyst is sulfated zirconia.

5. The method according to claim 1, wherein the γ,δ-unsaturated alcohol is 3-methyl-3-buten-1-ol.

6. The method according to claim 1, wherein the solid acid catalyst is aged by treatment at a temperature of 100 to 300° C. prior to dehydrating the γ,δ-unsaturated alcohol.

7. The method according to claim 1 wherein the dehydrating is conducted in an inert gas atmosphere.

8. The method according to claim 1, wherein the at least one solvent is selected from the group consisting of octane, nonane, decane, kerosene and liquid paraffins.

* * * * *